(12) United States Patent
Bahler et al.

(10) Patent No.: US 7,815,687 B2
(45) Date of Patent: Oct. 19, 2010

(54) METHOD OF PROMOTING CELL PROLIFERATION AND INGROWTH BY INJURY TO THE NATIVE TISSUE

(75) Inventors: Clinton D. Bahler, Indianapolis, IN (US); Alan R. Leewood, Lafayette, IN (US); Jichao Sun, West Lafayette, IN (US)

(73) Assignee: Med Institute, Inc., West Lafayette, IN (US)

( * ) Notice: Subject to any disclaimer, the term of this patent is extended or adjusted under 35 U.S.C. 154(b) by 61 days.

(21) Appl. No.: 12/337,163

(22) Filed: Dec. 17, 2008

(65) Prior Publication Data
US 2009/0157167 A1 Jun. 18, 2009

Related U.S. Application Data

(60) Provisional application No. 61/014,545, filed on Dec. 18, 2007.

(51) Int. Cl.
*A61F 2/06* (2006.01)
*A61F 2/00* (2006.01)

(52) U.S. Cl. ............... 623/23.74; 623/901; 606/200

(58) Field of Classification Search ... 623/23.71–23.76, 623/1.42–1.48
See application file for complete search history.

(56) References Cited

U.S. PATENT DOCUMENTS

| | | | |
|---|---|---|---|
| 4,271,839 A | 6/1981 | Fogarty et al. |
| 4,739,762 A | 4/1988 | Palmaz |
| 4,902,508 A | 2/1990 | Badylak et al. |
| 5,133,732 A | 7/1992 | Wiktor |
| 5,196,024 A | 3/1993 | Barath |
| 5,219,355 A | 6/1993 | Parodi et al. |
| 5,292,331 A | 3/1994 | Boneau |
| 5,331,975 A | 7/1994 | Bonutti |
| 5,421,955 A | 6/1995 | Lau et al. |
| 5,514,153 A | 5/1996 | Bonutti |
| 5,601,589 A | 2/1997 | Fogarty et al. |
| 5,643,208 A | 7/1997 | Parodi |
| 5,690,668 A | 11/1997 | Fogarty et al. |
| 5,733,337 A | 3/1998 | Carr, Jr. et al. |

(Continued)

FOREIGN PATENT DOCUMENTS

WO WO 98/22158 5/1998

OTHER PUBLICATIONS

Clapper, D., et al., "Covalently Immobilized ECM Proteins Improve Patency and Endothelialization of 4 MM Grafts Implanted in Dogs," *Trans Soc Biomat*, 16:42 (1993).

(Continued)

*Primary Examiner*—Suzette J Gherbi
(74) *Attorney, Agent, or Firm*—Brinks Hofer Gilson & Lione

(57) ABSTRACT

The present invention relates to methods of treating tissue of the human body, specially, methods of promoting cell proliferation and ingrowth around implantable medical devices. The methods include inserting an apparatus comprising asperities adapted to injure native tissue at a desired anchoring location, injuring the native tissue at the desired anchoring location with the apparatus to initiate an injury response in the native tissue to thereby promote cell proliferation and ingrowth; and implanting the medical device at the treatment location.

18 Claims, 6 Drawing Sheets

U.S. PATENT DOCUMENTS

| | | | |
|---|---|---|---|
| 5,891,030 | A | 4/1999 | Johnson et al. |
| 6,053,924 | A * | 4/2000 | Hussein ................. 606/108 |
| 6,090,127 | A | 7/2000 | Globerman |
| 6,169,917 | B1 | 1/2001 | Masotti et al. |
| 6,199,554 | B1 * | 3/2001 | Mann et al. ............. 128/898 |
| 6,206,931 | B1 | 3/2001 | Cook et al. |
| 6,514,271 | B2 * | 2/2003 | Evans et al. ............ 606/185 |
| 6,719,805 | B1 * | 4/2004 | Ahern .................. 623/23.74 |
| 6,743,232 | B2 * | 6/2004 | Overaker et al. ....... 623/13.14 |
| 6,782,284 | B1 | 8/2004 | Subramanyan et al. |
| 6,860,892 | B1 | 3/2005 | Tanaka et al. |
| 6,918,927 | B2 | 7/2005 | Bates et al. |
| 7,070,576 | B2 * | 7/2006 | O'Brien et al. ......... 604/96.01 |
| 7,153,315 | B2 * | 12/2006 | Miller .................. 606/159 |
| 7,204,847 | B1 * | 4/2007 | Gambale ............... 623/1.14 |
| 7,244,444 | B2 | 7/2007 | Bates |
| 7,279,002 | B2 * | 10/2007 | Shaw et al. ............ 623/1.11 |
| 7,645,272 | B2 * | 1/2010 | Chang et al. ........... 604/509 |
| 2004/0180042 | A1 | 9/2004 | Cook et al. |
| 2004/0199199 | A1 * | 10/2004 | Krolik et al. ........... 606/200 |
| 2004/0230220 | A1 | 11/2004 | Osborne |
| 2005/0033411 | A1 | 2/2005 | Wu et al. |
| 2005/0059890 | A1 | 3/2005 | Deal et al. |
| 2005/0187608 | A1 | 8/2005 | O'Hara |
| 2005/0261662 | A1 * | 11/2005 | Palasis et al. .......... 604/506 |
| 2005/0267513 | A1 | 12/2005 | Osborne |
| 2007/0049866 | A1 * | 3/2007 | Schwartz et al. ....... 604/93.01 |
| 2007/0255388 | A1 * | 11/2007 | Rudakov et al. ........ 623/1.11 |
| 2008/0077165 | A1 * | 3/2008 | Murphy ................ 606/159 |
| 2009/0163999 | A1 * | 6/2009 | Kaplan et al. .......... 623/1.16 |
| 2009/0227980 | A1 * | 9/2009 | Kangas et al. .......... 604/509 |
| 2010/0063582 | A1 * | 3/2010 | Rudakov ............... 623/1.16 |
| 2010/0069837 | A1 * | 3/2010 | Rassat et al. .......... 604/99.04 |

OTHER PUBLICATIONS

Heeschen, C., et al., "Nicotine Stimulates Angiogenesis and Promotes Tumor Growth and Atherosclerosis," *Nature Medicine*, 7(7):833-839 (2001).

Huynh, T., et al., "Remodeling of an Acellular Collagen Graft into a Physiologically Responsive Neovessel," *Nature Biotechnology*, 17:1083-1086 (1999).

Johnson, C., et al., "Matrix Metalloproteinase-9 Is Required for Adequate Angiogenic Revascularization of Ischemic Tissues, Potential Role in Capillary Branching," *Circulation Research*, 94:262-268 (2004).

Noordmans, H. and Smeulders, A., "High Accuracy Tracking of 2D/3D Curved Line-Structures by Consecutive Cross-Section Matching", *Pattern Recognition Letters*, 19(5):97-111 (1998).

Prinet, V., et al. "Vessels Representation in 2D and 3D Angiograms," *Computer Assisted Radiology and Surgery*, Elsevier Science, 240-245 (1997).

Tweden, K., et al., "Accelerated Healing of Cardiovascular Textiles Promoted by an RGD Peptide," *J. of Heart Valve Disease*, 4(1):S90-S97 (1995).

\* cited by examiner

A.    B.

A.    B.

METHOD OF PROMOTING CELL PROLIFERATION AND INGROWTH BY INJURY TO THE NATIVE TISSUE

RELATED APPLICATIONS

The present patent document claims the benefit of the filing date under 35 U.S.C. §119(e) of Provisional U.S. Patent Application Ser. No. 61/014,545, filed Dec. 18, 2007, which is hereby incorporated by reference.

BACKGROUND

1. Technical Field

The present invention relates to methods of treating tissue of the human body, specially, methods of promoting cell proliferation and ingrowth around an implantable medical device.

2. Background Information

Various medical conditions, including vascular disease, frequently require surgical intervention to repair tissue damage and facilitate healing. Such surgical repairs can include repairs with known medical devices. In most cases, these medical devices need to be inert to both body's immune system and its coagulation system: the implanted device will have to mimic the body to such a degree that it actually becomes invisible to the body's defense mechanisms. Medical devices, including artificial vascular grafts, stent grafts, and heart-valve sewing cuffs are examples of devices that remain in the body permanently and thus must be hemocompatible throughout their service life. However, the conventional practice of having highly polished implantable medical device surfaces results in the poor cell proliferation and ingrowth around the implanted medical device.

To ensure that the device is hemocompatible following implantation of the device, proliferation and ingrowth of endothelial and other existing cells located in or in the blood vessel wall or in the blood stream is important to the successful treatment of the given medical conditions.

Methods that utilize immobilizing agents, such as extracellular matrix (ECM) proteins and peptides, directly onto the device surface were previously suggested to promote the integration and adhesion of the native cells onto the implanted device. This technique has been shown to be effective in small-diameter (<6 mm) vascular grafts, for which it is desirable that a layer of endothelial cells cover the entire inner surface of the device to prevent occlusion (Clapper D L et al (Clapper D L, Hagen K M, Hupfer N M, et al., "Covalently Immobilized ECM Proteins Improve Patency and Endothelialization of 4-mm Grafts Implanted in Dogs," *Trans Soc Biomat*, 16:42, 1993, and Tweeden K S, Blevitt J, Harasaki H, et al., "RGD Modification of Cardiovascular Prosthetic Materials," in *Proceedings of the Cardiovascular Science and Technology Conference*, Arlington, Va., Association for the Advancement of Medical Instrumentation, p 124, December 1993). Although, some studies have demonstrated, for example, that an appropriate combination of covalently immobilized ECM proteins can improve both the patency and endothelialization of small diameter vascular grafts, with the mechanism of endothelialization most likely being via promotion of pannus ingrowth, these studies were limited to small diameter vascular grafts.

Also, blood-compatible biomimetic coatings were suggested to encourage the growth of a layer of endothelial cells over the device surface so that the blood is no longer exposed to the foreign material. However, device makers have been reluctant to adopt the coatings, due in part to the cost and complexity the coatings can add to the regulatory approval process. For example, U.S. Pat. Pub. 2005/0187608 A1 teaches that implantable intraluminal medical devices, such as stents, may be affixed with vascular endothelial growth factor, VEGF, which acts selectively on endothelial cells. Other factors that promote the stimulation of endothelial cells suggested as coatings for medical devices included members of the fibroblast growth factor family. Various agents that accelerate cellular migration, including agents that upregulate integrins, were also suggested to increase endothelialization. Nitric oxide and pro-angiogenic agent were also suggested to promote endothelialization Alternately, medical devices having, for example, nanotextured surfaces fabricated from a material, which by its physical material characteristics promotes the migration of endothelial towards the device were also suggested in the past.

We here provide an alternative reliable, simple and cost effective method of promoting cell proliferation and ingrowth around the implanted medical devices. The medical device implanted according to this method will be hemocompatible by becoming surrounded by the native tissue due to enhanced proliferation and ingrowth of the cells around the device, and especially at the anchoring location(s) of the device.

SUMMARY

In one embodiment, the invention relates to a method of promoting cell proliferation and ingrowth around an implantable medical device. The method comprises inserting an apparatus, comprising asperities adapted to injure native tissue at a desired anchoring location; injuring the native tissue with the apparatus at the desired anchoring location to thereby initiate an injury response in the native tissue to thereby promote cell proliferation and ingrowth; and implanting the device at the treatment location. The method may further include the step of inserting the apparatus to dislodge cellular debris at the desired anchoring location prior to injuring the native tissue. The apparatus may be integrated with a delivery system. The apparatus may be an inflatable device, such as a balloon. Alternatively, the apparatus may be a self-expandable device, such as stent or a filter. In certain embodiments, the apparatus may be a laser. The asperities may comprise sharp tips or blades. In one embodiment, the step of injuring comprises moving the apparatus proximally and distally at the anchoring location. In alternative embodiment, the step of injuring comprises rotational or "revolving" motion. The apparatus may comprise radiopaque material. The native tissue may be an aortic tissue. The device may be a stent, graft, or a stent graft. The device may include a naturally derived collagenous material, such as extracellular matrix (ECM) material.

In another embodiment, the invention relates to a method of promoting cell proliferation and ingrowth around a stent graft. The method includes inserting a balloon adapted for injuring the native tissue, such as cutting or scoring balloons, the balloon comprising asperities, such as blades or ridges, adapted to injure native tissue at a desired anchoring location; injuring the native tissue with the balloon at the desired anchoring location to thereby initiate an injury response in the native tissue to promote cell proliferation and ingrowth; and implanting the stent graft at the treatment location. The stent graft includes an extracellular matrix material, such as small intestine submucosa (SIS).

In another embodiment, the invention relates to a method of promoting cell proliferation and ingrowth around an implantable medical device to treat an aneurysm. The method comprises inserting an apparatus, comprising asperities adapted to injure native tissue at a desired anchoring location near the aneurysm; injuring the native tissue with the apparatus at the anchoring location near the aneurysm to thereby initiate an injury response in the native tissue to thereby promote cell proliferation and ingrowth; and implanting the device at an aneurysm location. The method may further include the step of inserting the apparatus to dislodge cellular debris at the desired anchoring location prior to injuring the native tissue. In certain embodiments, the step of injuring comprises moving the apparatus proximally and distally at the aneurysm location. The aneurysm may be an abdominal aortic aneurysm. In an alternative embodiment, the step of injuring comprises rotational or "revolving" motion. The apparatus may be integrated with a delivery system. The apparatus may be an inflatable device, such as a balloon. Alternatively, the apparatus may be a self-expandable device, such as a stent or a filter. In certain embodiments, the apparatus may be a laser. The device may include a naturally derived collagenous material, such as ECM.

In yet another embodiment, the invention relates to a method of promoting cell proliferation and ingrowth around a stent graft to treat an aneurysm. The method includes inserting a balloon, comprising asperitiess adapted to injure native tissue at a desired anchoring location near the aneurysm; injuring the native tissue with the balloon at the desired anchoring location to thereby initiate an injury response in the native tissue to thereby promote cell proliferation and ingrowth; and implanting the stent graft at an aneurysm location. The stent graft includes an extracellular matrix material, such as SIS.

In yet another embodiment, the invention relates to a method of promoting cell proliferation and ingrowth around an implantable medical device, comprising inserting an apparatus; over-extending the apparatus to cause an injury to the native tissue at a desired anchoring location to thereby initiate an injury response in the native tissue to promote cell proliferation and ingrowth; and implanting the device at the treatment location.

DETAILED DESCRIPTION OF THE DRAWINGS AND THE PRESENTLY PREFERRED EMBODIMENTS

Figure 1:
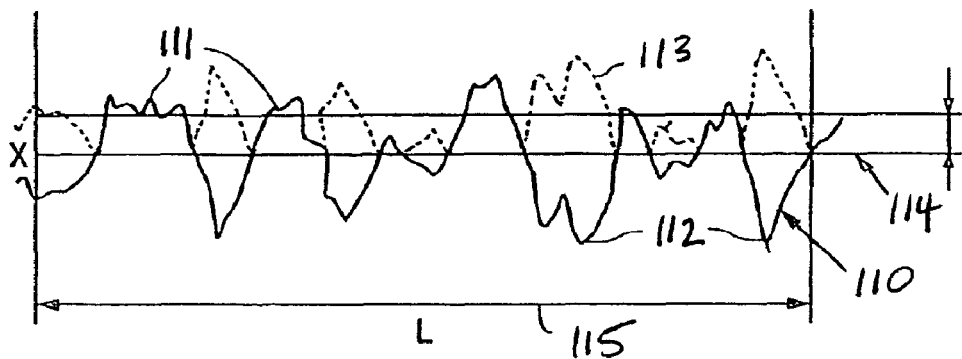
FIG. 1 graphically depicts elements used in determining the roughness factor, Ra, of a surface.

Unless defined otherwise, all technical and scientific terms used herein have the same meaning as commonly understood to one of ordinary skill in the art to which this invention belongs.

Described herein is a method of promoting cell proliferation and ingrowth around an implantable medical device. The method comprises inserting an apparatus, comprising asperities adapted to injure native tissue at a desired anchoring location. The method also comprises injuring the native tissue with the apparatus at the desired anchoring location to thereby initiate an injury response in the native tissue to thereby promote cell proliferation and ingrowth around the medical device. In certain instances, simultaneously or prior to injuring the native tissue, it may be desirable to dislodge and/or remove cellular debris (e.g., calcification) accumulated at the anchoring location. The method further includes implanting the medical device at a treatment location. As such, the term "treatment location" refers to an area of a tissue where the device is being implanted. Therefore, as described in detail below, by agitating or injuring the native tissue prior to the implantation of the medical device cell proliferation and ingrowth may be enhanced. As a result, endothelial cell proliferation and/or ingrowth around the device, and especially at the anchoring location(s), may be promoted or enhanced. The term "cell proliferation and/or ingrowth around the device" refers to cellular proliferation and/or ingrowth onto or on all or various sides of the medical device so to surround the device and make the medical device hemocompatible.

It is the endothelial cells that make the endothelium, which is a single layer of endothelial cells that forms the lining of all blood vessels. The endothelium regulates exchanges between blood and surrounding tissues and is surrounded by a basal lamina, i.e. extracellular matrix that separates epithelia layers and other cell types, including fat and muscle cells from connective tissue.

Endothelial cells cover or line the inner surface of the entire vascular system, including the heart, arteries, veins, capillaries and everything in between. Endothelial cells control the passage of materials and the transit of white blood cells into and out of the blood stream. While the larger blood vessels comprise multiple layers of different tissues, the smallest blood vessels consist essentially of endothelial cells and a basal lamina. Endothelial cells have a high capacity to modify or adjust their numbers and arrangement to suit local requirements. Essentially, if it were not for endothelial cells multiplying and remodeling, the network of blood vessel/tissue growth and repair would be impossible.

Even in an adult living organism, endothelial cells throughout the vascular system retain a capacity for cell division and movement. For example, if one portion of a vein or artery is missing endothelial cells through damage or disease, neighboring endothelial cells proliferate and migrate to the affected area in order to cover the exposed surface. Endothelial cells not only repair areas of missing endothelial cells, they are capable of creating new blood vessels. In addition, and directly related to the present invention, newly formed endothelial cells preferably cover implantable medical devices, including stents and other similar medical devices.

In certain instances, such as during a surgical repair of an aneurysm, such as an abdominal aortic aneurysm (AAA), injury may be created as a result of the surgical procedure itself, for example, by over-extending the vessel with a stent. However, in other types of endovascular repair, the implantable medical device, such as a stent graft, is often deployed into an artery with minimal injury to the arterial wall.

Although devices with barbs and hooks may cause more injury then those without, the injury caused by barbs and hooks may be too localized, insignificant and may not promote sufficient cell proliferation and ingrowth around the implantable medical device. In such instances, some form of agitation or injury to the native tissue that would result in inflammation (i.e., inflammatory response) of the tissue would be desired to promote cell proliferation and ingrowth around the implanted medical device.

To promote cell proliferation and ingrowth around an implantable medical device the native tissue may be injured or agitated prior to implantation of the device or by the implanted device itself. The injury or agitation of the native tissue at a desired anchoring location may be caused by moving an apparatus comprising asperities on its surface proximally and distally at the anchoring location. Alternatively, the injury or agitation of the native tissue at a desired anchoring location may be caused by rotational or "revolving" movements of the apparatus. Also, the injury may be caused by over-expanding the vessel wall with an apparatus. Also, the apparatus may be used to dislodge and/or remove cellular debris simultaneously with or prior to injuring the tissue. By dislodging the debris, the native tissue becomes exposed and available to injuring.

An apparatus that is integrated with a delivery system of the device may be used. Medical device delivery systems, including catheter systems, are known in the art and are described in more detail below. For example, the delivery system may include an outer sheath and an inner sheath, wherein the asperities may be placed on the surface of the inner sheath and exposed to the native tissue at an anchoring location once the outer sheath is appropriately withdrawn.

Another example of a preferred apparatus for use in the method of this invention includes an inflatable device, such as a balloon, which is known in the art. The balloon may be, for example, a cutting or a scoring balloon. Exemplary balloons were previously described in U.S. Pat. No. 4,271,839 to Fogarty et al., which discloses a balloon catheter with an inverted balloon and the entirety of which is expressly incorporated by reference herein. Similarly, U.S. Pat. Nos. 5,690,668 and 5,601,589, both by Fogarty et al., are also expressly incorporated by reference herein. U.S. Pat. Nos. 6,860,892, 5,643,208, and 5,219,355 describe additional examples of balloons and disclosures of these patents are incorporated by reference herein in their entirety. The apparatus may further include a fluid port in fluid communication with the inflatable balloon to supply inflation liquid to the inflatable balloon.

The apparatus may be expanded, for example by inflating to a predetermined shape and size (i.e., inflation volume) to radially compress against the lumen at the desired anchoring location. Preferably, the apparatus may expand to a shape and size specially designed for the anatomy of the region of the body in which the medical device will be implanted. Some exemplary ways to control the size and shape to which the apparatus, such as a balloon inflates are described below.

For example, because upon application of a given amount of force, a thinner material will stretch more than a thicker material, all other factors being equal, an inflatable device will stretch more where it is thinner and will stretch less where it is thicker. This is one way to control the shape into which a balloon expands when it is inflated. As an example, if a balloon has one half made of a very thick material and one half made of the same but much thinner material, the thin material will stretch more quickly and easily and the balloon will expand unevenly. The thin half of the balloon will expand more than the thicker material under the same pressure. The rate of expansion of different portions of the balloon may be controlled by using different materials or different thicknesses of materials. For example, if the balloon has portions formed of a thicker material and portions formed of a thinner material, the thinner portions will expand before the thicker portions expand. Consequently, native tissue may be injured in stages, or selectively as needed.

A second way to control the shape of expansion of the balloon is to use a fiber reinforced material. The direction of the fibers, along with their number, spacing, layering and length, controls the rate of expansion of the matrix material. Also, areas devoid of fibers will expand faster and/or further than areas which are reinforced. Specifically, the fibers resist stretching along their length. Thus, the balloon will stretch more in a direction across the fibers, or where the fibers are not present, than in a direction along the fibers. Fibers can be placed at the edge of the balloon to maintain the shape of the balloon when inflated. Fibers can be layered, with one layer in one direction and another layer in another direction, to control expansion in more than one direction. Adding fibers may make the balloon more puncture and tear resistant. For this purpose, the balloon can also be made of or include a self-sealing material.

A third way to control the shape of the balloon after inflation is to pre-shape the balloon to assume a certain form when expanded. This may be done in a molding process. For example, the balloon may be formed on a mandrel which is of a particular shape and which is sized about halfway between the unexpanded and the desired expanded size of the balloon.

Another way to achieve shape control is to fix tethering cords to portions of the balloon in order to control and/or limit the expansion of the balloon. Yet another way is to add a plate which limits the shape of the balloon. For example, if a flat plate is added to a portion of the surface of the balloon, the flat plate will remain flat and result in a flat area on one side of the balloon when inflated. The balloon can have multiple such plates to create specific shapes.

Accordingly, the balloon itself can be round, eccentric, oval, conical, wedge-shaped, U-shaped, curved, angled, or it may be in any shape desired for the particular anatomy and application. The balloon may be irregularly shaped when inflated such that it expands more in an area where the surgeon desires to cause more injury. For further detail about the various types of balloons, balloon materials, balloon sizes and balloon shapes which may be used according to the methods of this invention, see U.S. Pat. Nos. 5,514,153 and 5,331,975, which are incorporated by reference herein in their entirety.

To determine the inflation volume of an inflatable apparatus, it is possible to use image data generated by computed tomography (CT) for vessel or lumen diameters and have chart for volume of air to add to reach a specific diameter. For example, if an apparatus is to be inserted at an abdominal aortic aneurysm location, proximal aortic (just below the renal arteries) and iliac artery diameters measurements may be desired. A method and apparatus for assisting an associated user in planning a stent placement of a blood vessel in a patient using CT scans were previously described U.S. Pat. No. 6,782,284, disclosure of which is incorporated herein by reference in its entirety. In short, a three-dimensional vascular image may be acquired that includes imaging of the vessel to be treated. The vessel to be treated may be tracked in the three-dimensional vascular image. The vessel tracking may include at least extraction of a vessel centerline and vessel boundaries.

Other imaging techniques, such as magnetic resonance-based imaging (MRI) or nuclear medicine, may also be used to determine the inflation volume (Noordmans, et al. "High Accuracy Tracking of 2D/3D Curved Line-Structures by Consecutive Cross-Section Matching", Pattern Recognition Letters, vol. 19, No. 5, pp. 97-111, 1998; Prinet, et al. "Vessels Representation in 2D and 3D Angiograms", CAR '97 Computer Assisted Radiology and Surgery, Lemke, et al., Elsevier Science, pp. 240-245, 1997).

Another example of a system for two dimensional and three dimensional imaging of tubular structures in the human body was previously described in U.S. Pat. No. 5,891,030, disclosure of which is incorporated herein by reference in its entirety. A method and device for reconstructing three-dimensional images of blood vessels, particularly coronary arteries, or other three-dimensional structures were previously described in U.S. Pat. No. 6,169,917, disclosure of which is incorporated herein in its entirety.

In certain embodiment, the apparatus for use in the method of this invention includes a cutting balloon. U.S. Pat. No. 5,196,024, which issued to Barath on Mar. 23, 1993 for an invention entitled "Balloon Catheter With Cutting Edge," discloses an inflatable angioplasty balloon having a number of elongated atherotomes (e.g. 8 blades) mounted longitudinally on the surface of the balloon and distributed uniformly around the circumference of the balloon. During an inflation of the Barath balloon, the atherotomes move radially to induce a series of longitudinal cuts into the surface of the artery that are somewhat uniformly distributed around the circumference of the artery. U.S. Pat. No. 7,070,576 describes yet another example of a cutting balloon, where either a single incising element (i.e. cutting blade) or a plurality of incising elements (e.g. three elongated cutting blades) is mounted longitudinally on the outer surface of the balloon with the incising elements circumferentially spaced-apart. Incising elements may be blades, wires and other suitable structures.

In further embodiment, the apparatus for use in the method of this invention may be any self-expandable device, such as a stent. Various types of stents are known in the art and would be suitable for use as the apparatus for agitating tissue.

In other embodiments, the apparatus for use in the method of this invention may be a filter, such as a vena cava filter. U.S. Pub. Nos. 2004/0230220 and 2005/0267513, which are incorporated by reference herein in their entirety, describe exemplary vena cava filters.

In yet another example, an apparatus for use to agitate the tissue and/or dislodge and/or remove the cellular debris from the vessel may be a laser. Suitable lasers for use in the method described herein will be known to those skilled in the art.

In some instances, the outer surface of the apparatus comprises asperities that provide for roughened, uneven, unsmooth, or textured outer surface of the apparatus. The asperities may cause the designated region of the apparatus to have a roughness factor, Ra. The roughness factor is used to quantify the surface roughness. The roughness factor may vary depending on the intended use of the intended use of the apparatus. Specifically, the roughness factor may be different when the apparatus is used to dislodge and/or remove cellular debris and different when the apparatus is used to injure the native tissue exposed by removal of cellular debris. In any event, the roughness factor will be sufficient to dislodge and/or remove the cellular debris and injure the tissue to induce inflammation of tissue at the anchoring location.

Alternatively, an injury to the vessel may be induced by simply over-expanding it by less than about 10-12% of the normal diameter of the vessel. Stretching the vessel will damage the tissue inciting the healing response. However, over-expanding the vessel to the point where dissection of the vessel becomes critical should be avoided. For example, over-expanding beyond approximately 10-12% greater than nominal diameter of the vessel should be avoided.

In FIG. 1, a surface having asperities is outlined in two-dimensions by the profile 110. Profile 110 outlines irregular protrusions 111 and indentations 112 of a surface having asperities. The roughness factor, Ra, is defined herein as the arithmetic means of the absolute value of the profile departures 113 from a centerline 114 through profile 110, within an evaluation length 115. Typically, the asperities formed by the methods described below cause the designated region of the apparatus to have a roughness factor, Ra, greater than about 100 nm. For a three-dimensional surface, centerline 114 becomes a mean plane and Ra is defined as the arithmetic mean of absolute values of the surface departures from the mean plane within an evaluation area. The digital approximation for the three dimensional Ra over an evaluation area is given by Equation 1:

$$Ra = \frac{1}{MN}\sum_{j=1}^{M}\sum_{i=1}^{N}|Z_{ij}|$$ Equation 1

M and N are the number of data points in the X and Y directions, respectively, of the evaluation area, and Z is the surface height of each point relative to the mean plane.

The roughness factor, Ra, of asperities on an apparatus within the present invention may be measured, for example, by using a commercially available Veeco Metrology Group (Tucson, Ariz.) WYKO NT-2000 system, which is non-contact optical profiler. VSI (vertical scanning interferometer) mode may be used. A low pass filter may be used, which removes the effects of high spatial frequency roughness, smoothing over the features that are smaller then a nine pixel window. A 50× objective and 2.0×F0V sense may be used to produce an effective magnification of 100×. This objective and converter combination profiles a 0.58 μm×0.44 μm evaluation area, at a spatial sampling interval of 159.13 nm. For statistical purposes, samples are measured at five separate locations. Equation 1 is used to calculate the value of Ra.

Figure 2A:
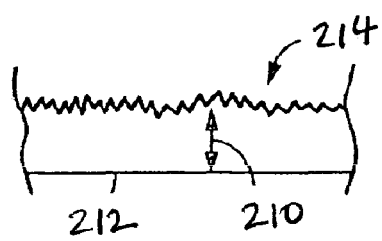
FIGS. 2A, 2B, 2C, 2D, 2E, 2F and 2G are cross-sectional views of portions of an apparatus with exemplary asperities.
Figure 2B:
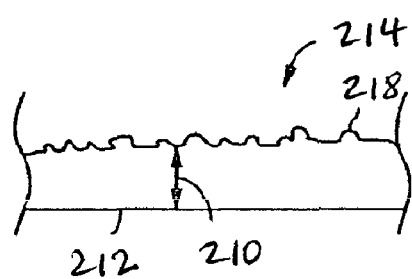
Figure 2C:
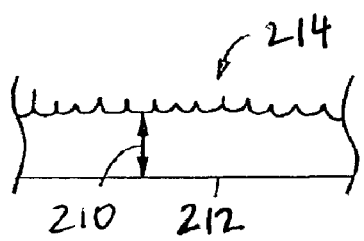

The term "asperities" refers to any projections, protrusions, bulges, indentations, etc. from a surface of an apparatus used to intentionally injure or agitate native tissue. In general, the asperities on the surface of the apparatus may have a variety of shapes, examples of which are illustrated in cross-sectional views of the apparatus of FIGS. 2A-2E. Outer surface asperities 214 may be random and irregular, as exemplified in FIGS. 2A and 2B. The asperities 214 may also be more regular and well-defined, as exemplified in FIGS. 2C, 2D, and 2E. The asperities of the embodiments may be formed by protrusions and indentations in the surface that may have a variety of shapes and sizes, for example, the rounded shape 218 of FIG. 2B, the pointed shape 219 of FIG. 2D, or the rectangular shape 215 of FIG. 2E. In the exemplary surface of FIG. 2E, the protrusion and indentations may cause the surface to have ridges 216 and channels 217. The protrusions and indentations may also have different densities on the surface, as illustrated by the difference between FIGS. 2C and 2D.

Figure 2D:
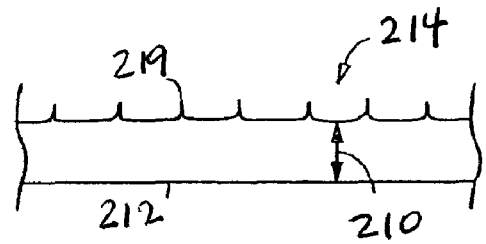
Figure 2E:
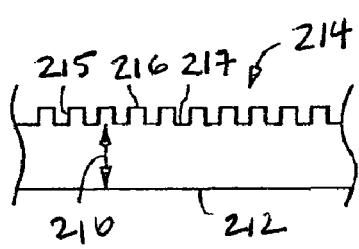
Figure 2F:
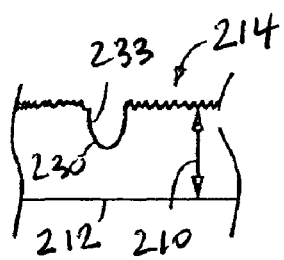
Figure 2G:
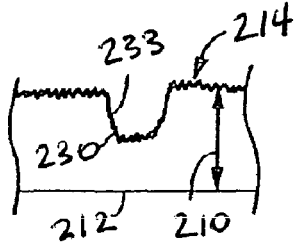

Preferably, the asperities are sharp, having, for instance, sharp protrusions as in 219, FIG. 2D, or sharp edges, to dislodge and/or remove cellular debris, and agitate or injure the native tissue at a desired anchoring location once the apparatus is inserted, and in the instance of an inflatable apparatus, further inflated and expanded. In certain embodiments, the asperities may be blades, wires and/or any other suitable structures. The agitation or injury may involve moving the apparatus proximally and distally or by rotating the apparatus at the anchoring location of the native tissue. Alternatively, the injury may occur by intentional over-expanding the vessel. The term "injury" refers to an intentional injury and an injury with intent to create healing response. This agitation or injury to the native tissue may enhance the ability of the cells to proliferate and ingrow around the implantable medical device implanted following agitation and injury with the apparatus comprising asperities on its surface.

A. Mechanical Methods for Creating Asperities

A variety of methods can be used to create the asperities on the outer surface of the apparatus. Exemplary methods of creating asperities on medical devices were previously described in U.S. Pat. Pub. No. 2005/0033411, or U.S. Pat. No. 6,918,927, disclosures of which are incorporated by reference herein in their entirety.

Figure 3A:
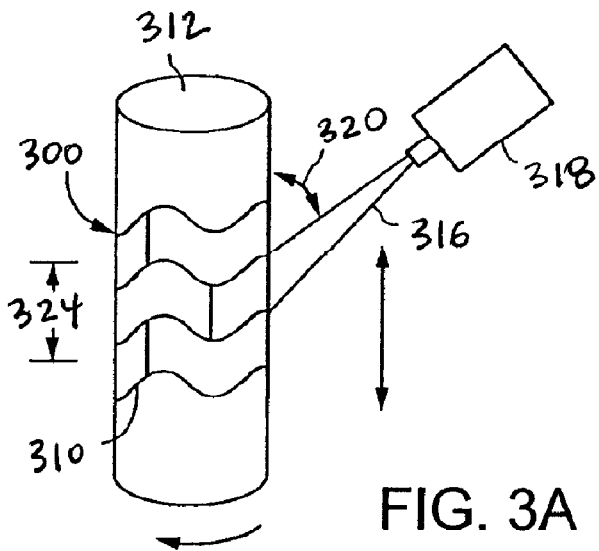
FIG. 3A is a schematic representation of the method of using a pressurized grit source to create asperities on the outer surface of an apparatus used to agitate or injure the native tissue prior to implantation of a medical device.

For example, FIG. 3A illustrates one embodiment, in which a pressurized stream of grit material may be directed upon the outer surface 310 of an apparatus 300 to create asperities on the outer surface of the apparatus. Examples of such processes include bead blasting and sand blasting. Bead blasting refers to the use of pressurized gas to project beads of a relatively uniform diameter at an object at a high velocity. The bead may be made of a variety of materials, such as latex, aluminum oxide, or silicon oxide. In sand blasting, the grit projected does not have as uniform a diameter as in bead blasting. Both bead blasting and sand blasting are techniques that are well known in the art.

In FIG. 3A, the apparatus 300, is mounted onto a mandrel 312. The apparatus may then be rotated while the grit 316, e.g. beads, is projected at the apparatus' outer surface from the pressurized grit source 318. The grit may be projected at the apparatus, for example, at an approximately 30° angle 320 to the vertical axis of the apparatus, and is passed up and down over the outer surface 310 of the apparatus until the desired pattern, type, and number of asperities have been created. The visual appearance of the surface can be used to indicate that it is roughened appropriately. The outer surface of the apparatus becomes dull, non-reflective, and darker in color after the roughening process. Subsequently, the apparatus may be removed from the mandrel and cleaned, for example by immersion and sonication in an isopropyl alcohol bath for approximately 20 minutes.

The roughness factor achieved using a pressurized grit source may be controlled by the size of the grit, e.g., the diameter of the beads, the pressure used, the distance between the grit source and the apparatus surface, and the length of time the grit is blasted at the surface. By way of example and not limitation, the grit can be beads having a diameter of between 10 µm and 50 µm. Pressures of 30 PSI (pounds per square inch) to 60 PSI can be used to project the beads from a distance of approximately 3-10 cm from the apparatus. The grit source may be passed very quickly, in approximately 1-3 seconds, down and up over the apparatus' outer surface. The apparatus may then be rotated 120° and the process repeated at least twice so the entire apparatus is roughened.

Figure 3B:
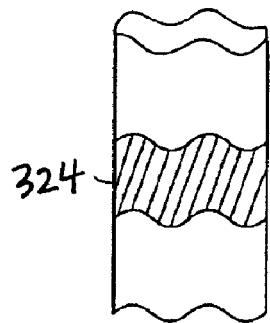
FIG. 3B is a schematic representation of an apparatus having asperities on a middle portion.
Figure 3C:
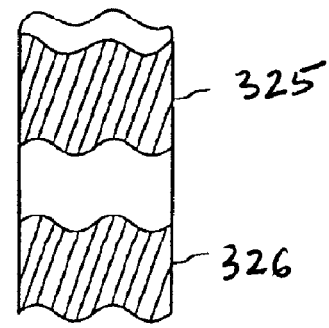
FIG. 3C is a schematic representation of an apparatus having asperities adjacent to the ends of the apparatus.

In one embodiment, the entire outer surface need not be roughened. For example, the grit may be projected at only a middle region 324 (FIGS. 3A and 3B) of the apparatus, so that the asperities are formed only in a middle region of the apparatus' outer surface, and not adjacent to the opposing ends of the apparatus, FIG. 3B. Or, as illustrated in FIG. 3C, the grit may be projected only at the ends of the apparatus, to create asperities at one or both ends, 325 and 326.

In another embodiment, the asperities may be formed by grinding the apparatus between two sanding plates or using sandpaper to scratch the outer surface. In this method, the roughness factor achieved depends on the grain size of the surface of the sanding plates. This method may be particularly useful with polymer apparatuses made from relatively soft materials.

B. Creating Asperities by Removal of Apparatus Material

In another embodiment, chemical etching may be used to create asperities on the outer surface of a apparatus. Chemical etching methods are known to those of ordinary skill in the art. The chemical etchant solution typically includes an acid that degrades and dissolves the material from which the apparatus is made. The chemical etchant may be applied to the outer surface, and then rinsed off of the surface after a predetermined period of time. The length of time the etchant may be left on the surface depends on the etch rate and the depth of etch desired.

The roughness factor produced by the chemical etchant depends on the method of application of the etchant. In one embodiment, the chemical etchant may be applied to the apparatus outer surface with a fine sponge or by spraying a mist of the chemical etchant onto the apparatus. The chemical etchant may be rinsed off of the apparatus, leaving a rough outer surface. The roughness factor will depend on the apparatus material and the chemical etchant used, the amount and length of time the etchant was applied, and how the etchant was applied.

In one embodiment, a patterned mask that has openings may be applied to the apparatus outer surface before the chemical etchant is applied. The etchant is then applied in a uniform manner and allowed to etch the apparatus material through the openings of the mask. The use of patterned masks with chemical etchants is known to those of ordinary skill in the art. The mask may typically be applied to a flat piece of the apparatus material and the resulting outer surface pattern etched into the surface. Then, the flat piece of apparatus material may be cut and formed into the apparatus.

In this embodiment, the patterned mask may be used to make asperities that are composed of more regular and well-defined shapes. The shapes can be chosen depending on the eventual application of the apparatus and anatomy. In one example, a patterned masking followed by etching is used to create asperities composed of relatively sharp tips (219 of FIG. 2D), or ridges and channels (216 and 217, respectively, of FIG. 2E). The sharp tips 219 may have a height between 0.1 µm and 10 µm or at least 0.1 µm. The sharp tips can be of any density on the surface, although a higher density has more tips to penetrate the tissue.

If, when creating the asperities by chemical etching, a significant amount of apparatus material is removed, a thicker material may be used to form the apparatus.

In other embodiments, asperities are formed by machining or laser cutting the outer surface. These methods may also be used to make asperities composed of more regular and well-defined shapes. For example, a laser discharge machine tool may be programmed to cut a desired pattern into the outer surface of an apparatus.

C. Creating Asperities by Adding Material

In another embodiment, additional material may be deposited onto the outer surface of the apparatus to create the asperities. In one method, the additional material, which is typically a metal, is first made into a powder. The powder particles may be then bonded to the outer surface to form the asperities. Methods of making metal powder are known in the art. For example, the powder may be made by grinding the metal to form particles of a predetermined size. The particles may then be put onto the outer surface of the apparatus, for example, by rolling the apparatus in the powdered metal or spaying the powdered metal onto the apparatus. The apparatus may be electrostatically charged to a charge, typically negative, that is opposite that of the powdered metal, to improve the adhesion of the powder to the apparatus.

In one embodiment, depending on the material that makes up the outer surface of the apparatus, the apparatus coated with the particles may be heated to weld the particles to the apparatus by sintering in a furnace or with a flame. These methods are known to those of skill in the art. Typically, the apparatus material, particle material, and sintering temperature are chosen so that melting temperatures of the materials allow the particles to be welded to the apparatus without distortion of the apparatus by the heat treatment. For example, the apparatus material may be PET or nylon and the particles may be gold, aluminum, or copper.

A temporary coating may also be used on the outer surface of the apparatus if it is desired to create asperities on only designated regions of the outer surface. For example, if it is desired to have the asperities adjacent to the ends of the apparatus (as illustrated in FIG. 3C), the temporary coating can be applied to the middle portion of the apparatus before the particles are applied to the apparatus.

Figure 4:
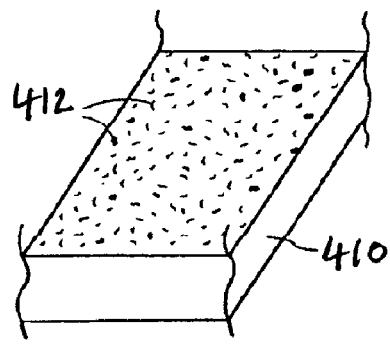
FIG. 4 is a perspective view of a portion of an apparatus with asperities on the top surface deposited by sputtering material onto the top surface.

Additional material may also be added via physical deposition processes, for example, sputtering, which is known to those of ordinary skill in the art. In sputtering, an energy beam, for instance an ion beam, is directed at a target formed of the material which is to be deposited on the substrate. The energy beam dislodges atoms of the target material. The target material atoms are transported to the substrate, which in this instance is the apparatus on which asperities are being formed. Once at the substrate, the atoms form "islands", or small nodules of the deposition material on the substrate. FIG. 4 illustrates the "islands" 412 formed on an illustrative portion of the substrate 410, corresponding to the apparatus outer surface (210 of FIG. 2).

Conventionally, sputtering is used to form a thin film of the deposition material over the substrate, and sputtering conditions are used such that the "islands" grow, spread, and condense on the substrate to form a thin film. To form the asperities, however, the sputtering process conditions are set so that instead of creating a uniform film over the substrate, the "islands" do not grow, spread, and condense, leaving a rough surface. Process conditions in which a lower pressure and shorter deposition time than is typically used for thin film deposition are used to form the asperities.

Typically, an apparatus is inserted into the sputtering chamber and rotated while material is deposited on the outer surface. Alternatively, material may be deposited onto the flat piece of apparatus material before it is cut and formed into the apparatus.

The sputtering, however, may only loosely deposit the material onto the outer surface of the apparatus. In such cases, to further enhance attachment of the deposited material to the substrate, a heat treatment, for instance sintering can be performed. As discussed above, the temperature ranges for heating may depend on the deposition material and the apparatus material.

In certain embodiments, objects such as wires or blades may be deposited or attached to the surface of the apparatus. Preferably, the roughened, uneven, unsmooth, or textured surface of the apparatus is created.

In one embodiment, radiopaque materials may also be deposited on the apparatus, to not only create asperities on the apparatus, but to allow visualization of the apparatus after insertion into the desired anchoring location within the patient's body. For example, the radio-opaque material can be applied adjacent to the ends of the apparatus.

Method

The first step in the method for promoting cell proliferation and ingrowth around an implantable medical device includes inserting an apparatus, such as one described above, comprising asperities to a desired anchoring location in a patient's body. The apparatus may be inserted using a delivery system, such as a catheter system known in the art. In one embodiment, the apparatus may be integrated with the delivery system. The catheter and the apparatus are advanced through a lumen of the patient's body until the proximal portion of the apparatus (for example, the balloon portion) is positioned adjacent to the desired anchoring location. The "desired anchoring location" refers to any lumen, duct, organ, vessel, other bodily passage or cavity or a pathway leading thereto in which wire guide/guiding member access is maintained throughout a particular procedure or series of procedures. In one embodiment, the desired anchoring location may also be an entire treatment location.

In one embodiment, a system for introducing multiple medical devices may be used. For example, a system for introducing multiple medical devices, e.g. catheter into lumen of patient, having wire guide and a medical device including respective indicators which are monitored to determine whether guide has moved to uncoupled position, such as described in U.S. Pat. Pub. No. 2005/0059890 A1, which is incorporated by reference in its entirety, may be used.

Following the appropriate placement of the apparatus at the desired anchoring location, the native tissue may be injured with the apparatus to thereby initiate an injury response in the native tissue to thereby promote cell proliferation and ingrowth around an implantable device. For example, once in place, the apparatus may be expanded or inflated and then may be compressed or deflated to a smaller profile to allow the catheter to be withdrawn away from the anchoring location. Next, the apparatus may be expanded or inflated and moved proximally and distally against the lumen's wall or may be rotated to cause injury to the native tissue with the asperities located on the outer surface of the apparatus. Alternatively, the expanded or inflated apparatus may be rotated around the axis to cause injury at the desired anchoring location.

In certain embodiments, the apparatus may be used to dislodge and/or remove cellular debris. Dislodging or removal of the cellular debris may be desired prior to causing the injury to the native issue. Removal of cellular debris allows the native to be exposed and available for injury. Same or different apparatus may be used to remove cellular debris and to injure or agitate the tissue.

The extent of injury is preferably determined by previous animal and pre-clinical studies and monitoring may not be required.

Figure 5:
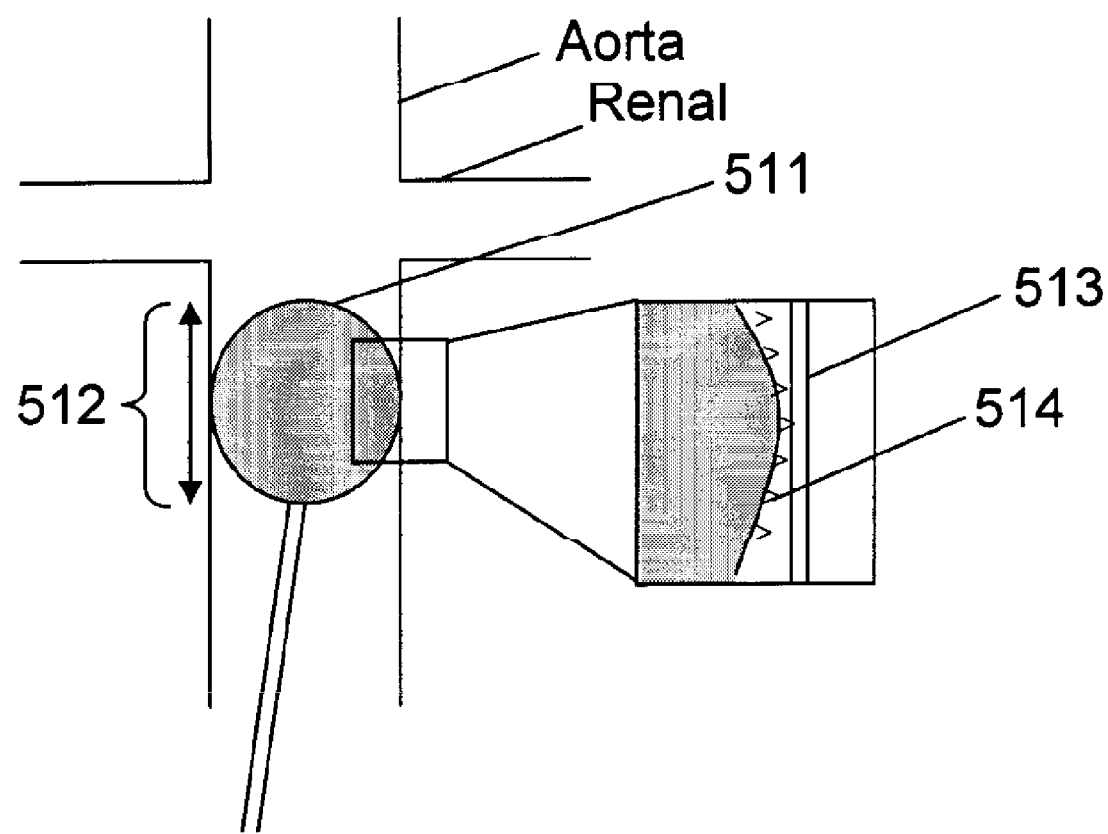
FIG. 5 is a schematic illustration of an apparatus inserted at a desired anchoring location to agitate and injure the native tissue.

Because most endovascular abdominal aneurysm devices, such as stent grafts, come in contact with the arterial wall at the proximal neck and distal end of the stent-graft, tissue ingrowth may be desired in these two locations (anchoring locations). To promote tissue ingrowth in these two anchoring locations, it may be advantageous to agitate or create injury to native tissue in these specified areas. As illustrated in FIG. 5, an apparatus, such as inflatable balloon 511 comprising asperities 514 is inserted to cause injury at the desired anchoring locations near an aortic abdominal aneurysm 512, prior to implantation of the medical device, such a stent graft. The balloon 511 may be inflated and moved along the arterial wall 513 (arrow) to cause injury to the native tissue.

Once the injury to the native tissue is created at the desired anchoring location(s), the apparatus may be compressed or deflated and may be removed from the patient's body. Following the removal of the apparatus, an implantable medical device, such as a stent, graft or a stent graft, appropriate for the treatment of the specific medical condition, may be implanted at a treatment location in the patient's body. Preferably, the implantable medical device is inserted though the same catheter system used to insert the apparatus. Once at the desired treatment location, the device is deployed and the catheter assembly is removed from the patient's body.

In an alternative embodiment, the apparatus may not be removed prior to the implantation of the medical device. For example, if the apparatus is integrated with the delivery system, the medical device may be implanted immediately after the injury to the tissue is created and prior to the removal of the delivery system. Once the medical device is implanted at the treatment location, the apparatus integrated with the delivery system may be removed from the patient's body.

As mentioned above, following the injury or agitation, a medical device may be implanted. Any suitable implantable medical device, such as a stent, graft, stent graft or other device, may be used. The choice of the device is depended upon the anatomy and the specific condition to be treated. Other factors may also play a role.

FIG. 6 illustrates one exemplary medical device, such as a stent 600 that may be implanted in accordance with one embodiment of this invention. Stents are scaffoldings, usually cylindrical or tubular in shape, which are inserted into an anatomical passageway and operate to physically hold open and, if desired, to expand or replace the wall of the passageway. Stents are capable of being compressed for insertion through small cavities via balloon-catheters, positioned in the desired treatment location, then expanded to a larger diameter. Stents can be either balloon-expandable or self-expandable.

One example of a stent is a self-expanding stainless steel stent for percutaneous implantation sold under the tradename ZENITH®, commercially available from Cook, Incorporated (Bloomington, Ind.). Other examples include a Wallstent variety stent, Cook-Z® Stent or Zilver Stent. Some exemplary stents are disclosed in U.S. Pat. Nos. 5,292,331, 6,090,127, 5,133,732, 4,739,762, and 5,421,955.

Figure 6A:
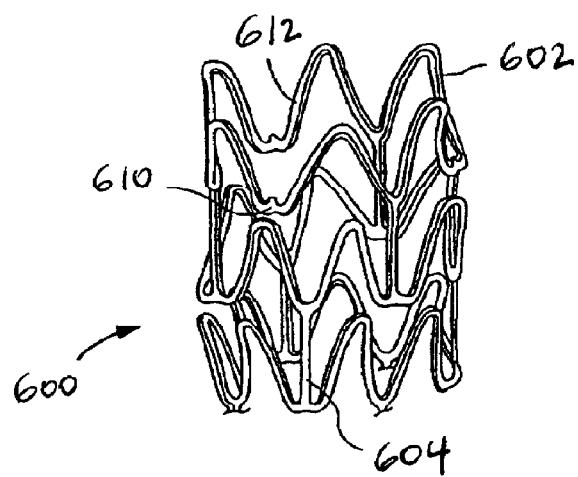
FIG. 6A is a perspective view of an example of a stent in an expanded state.

Referring to FIG. 6A, exemplary stent 600 is a patterned tubular device that includes a plurality of radially expanding cylindrical struts 602 disposed generally coaxially and interconnected by connecting struts 604 that are disposed between and connect adjacent cylindrical struts 602. Struts 602 and 604 can be any suitable thickness T between the stent outer surface 610 and inner surface 612. Typically thickness T is in the range of approximately 50 μm (0.002 inches) to 200 μm (0.008 inches). A specific choice of thickness depends on the anatomy and size of the target lumen. As used in this specification, the terms "lumen" or "body passageway" are intended to have a broad meaning and encompasses any duct (e.g., natural or iatrogenic) within the human body and can include a member selected from the group comprising: blood vessels, respiratory ducts, gastrointestinal ducts, and the like.

Figure 6B:
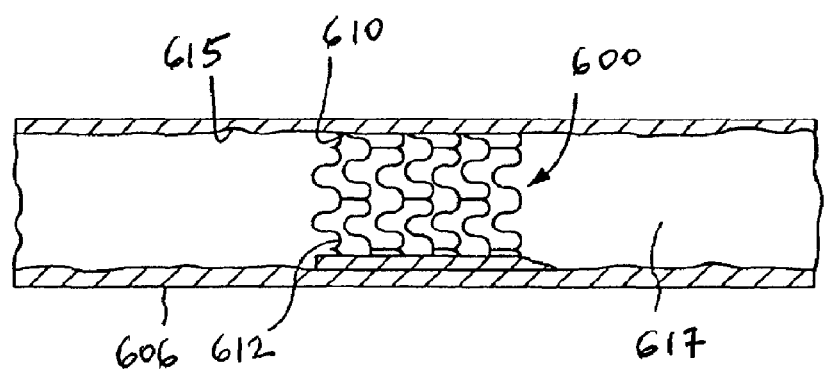
FIG. 6B is a cross-sectional side view of a stent implanted in a lumen.

FIG. 6B illustrates stent 600 of FIG. 6A implanted in a lumen 606. The stent struts 602 and 604 define a stent body having an outer surface 610 in contact with inner surface of the lumen 615, and an inner surface 612 in contact with the fluid stream through the lumen 617. For example, when stent 600 is implanted in a blood vessel, the outer surface is in contact with the blood vessel wall, and the inner surface is in contact with the blood flowing through the vessel.

Figure 6C:
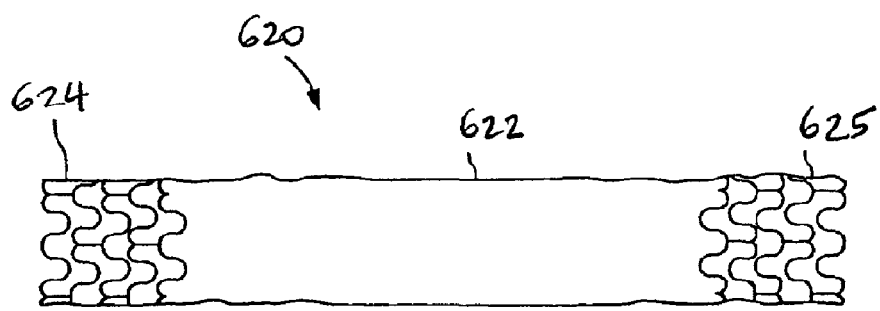
FIG. 6C is a side view of a graft.
Figure 6D:
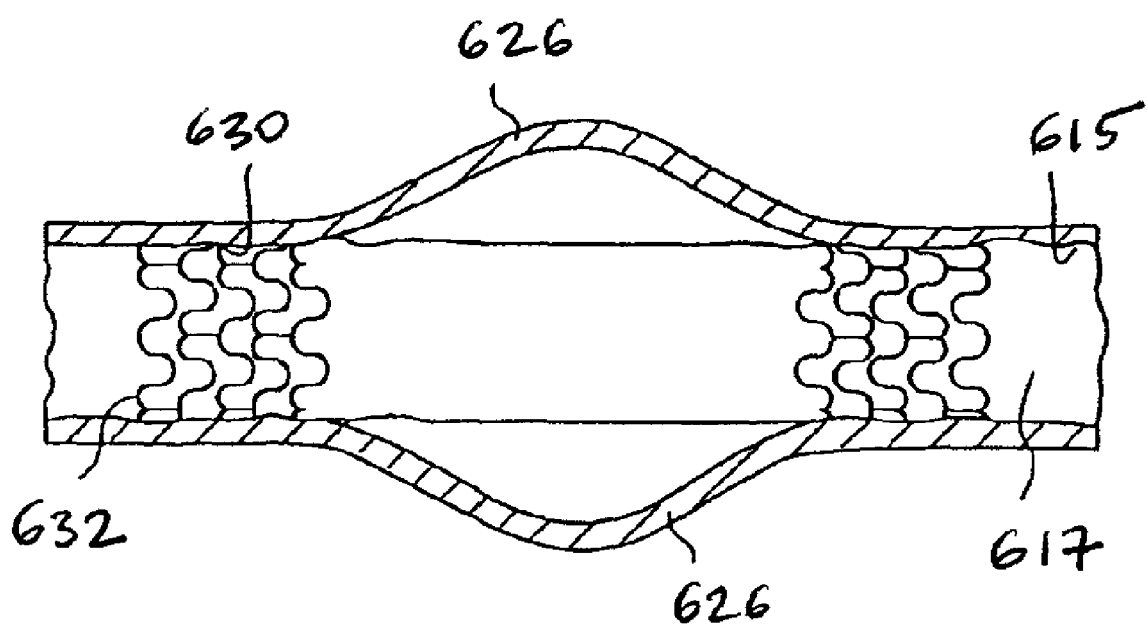
FIG. 6D is a cross-sectional side view of a graft implanted in a damaged vessel.

An exemplary graft 620 is illustrated in FIG. 6C. Grafts are typically placed in a blood vessel to either replace a diseased segment that has been removed, or, as illustrated in FIG. 6D, to form a bypass conduit through a damaged segment of the vessel wall, for instance, an aneurysm 626. The graft 620 has a tubular portion 622, which spans the site of the damaged tissue and through which the blood flows. The graft has sections, 624 and 625, at both ends of tube 622 that are used to secure the graft to the inside of the vessel wall 615. The graft also has an outer surface 630, portions of which are in contact with inner surface of the blood vessel wall 615, and an inner surface 632, in contact with the blood flowing through the vessel 617.

In additional embodiments, use of other implantable devices that would benefit from enhanced cellular perfusion and anchoring is also contemplated.

For example, in certain embodiments, the device for implantation once the injury is the tissue is created may be a stent graft.

Preferably, the device includes naturally derived collagenous material, such as extracellular matrix (ECM) material to further accelerate or promote cellular ingrowth or proliferation already enhanced or induced by the inflammatory response resulting from the injury to the tissue.

The naturally derived collagenous material may be incorporated into the device by coating, stitching, applying, weaving in, impregnating, making, forming or otherwise incorporating the naturally derived collagenous material into the device. For example, a sent may be coated with the naturally derived collagenous material. In another example, a graft material may be impregnated with the naturally derived collagenous material (see, e.g., U.S. Pat. No. 7,244,444, incorporated herein by reference in its entirety).

Naturally derived collagenous materials that are at least bioresorbable will provide advantage in the present invention, with materials that are bioremodelable and promote cellular invasion and ingrowth providing particular advantage. For example, these materials provide improved device fixation and sealing, as illustrated below in the Examples section.

Suitable bioremodelable materials may be provided by collagenous ECM possessing biotropic properties, including in certain forms angiogenic collagenous ECMs. For example, suitable collagenous materials include ECMs such as submucosa, renal capsule membrane, dermal collagen, dura mater, pericardium, fascia lata, serosa, peritoneum or basement membrane layers, including liver basement membrane. Suitable submucosa materials for these purposes include, for instance, intestinal submucosa, including small intestinal submucosa, stomach submucosa, urinary bladder submucosa, and uterine submucosa.

As prepared, the submucosa material and any other ECM used may optionally retain growth factors or other bioactive components native to the source tissue. For example, the submucosa or other ECM may include one or more growth factors such as basic fibroblast growth factor (FGF-2), transforming growth factor beta (TGF-beta), epidermal growth factor (EGF), and/or platelet derived growth factor (PDGF).

As well, submucosa or other ECM used in the invention may include other biological materials such as heparin, heparin sulfate, hyaluronic acid, fibronectin and the like. Thus, generally speaking, the submucosa or other ECM material may include a bioactive component that induces, directly or indirectly, a cellular response such as a change in cell morphology, proliferation, growth, protein, or gene expression.

Submucosa or other ECM materials may be derived from any suitable organ or other tissue source, usually sources containing connective tissues. The ECM materials processed for use in the invention will typically include abundant collagen, most commonly being constituted at least about 80% by weight collagen on a dry weight basis. Such naturally-derived ECM materials will for the most part include collagen fibers that are non-randomly oriented, for instance occurring as generally uniaxial or multi-axial but regularly oriented fibers. When processed to retain native bioactive factors, the ECM material can retain these factors interspersed as solids between, upon and/or within the collagen fibers. Particularly desirable naturally-derived ECM materials for use in the invention will include significant amounts of such interspersed, non-collagenous solids that are readily ascertainable under light microscopic examination with specific staining. Such non-collagenous solids can constitute a significant percentage of the dry weight of the ECM material in certain inventive embodiments, for example at least about 1%, at least about 3%, and at least about 5% by weight in various embodiments of the invention.

The submucosa or other ECM material used in the present invention may also exhibit an angiogenic character and thus be effective to induce angiogenesis in a host engrafted with the material. In this regard, angiogenesis is the process through which the body makes new blood vessels to generate increased blood supply to tissues. Thus, angiogenic materials, when contacted with host tissues, promote or encourage the infiltration of new blood vessels. Methods for measuring in vivo angiogenesis in response to biomaterial implantation have recently been developed. For example, one such method uses a subcutaneous implant model to determine the angiogenic character of a material. See, C. Heeschen et al., *Nature Medicine* 7 (7):833-839 (2001). When combined with a fluorescence microangiography technique, this model can provide both quantitative and qualitative measures of angiogenesis into biomaterials. C. Johnson et al., *Circulation Research* 94(2):262-268 (2004).

Further, in addition or as an alternative to the inclusion of native bioactive components, non-native bioactive components such as those synthetically produced by recombinant technology or other methods, may be incorporated into the submucosa or other ECM tissue. These non-native bioactive components may be naturally-derived or recombinantly produced proteins that correspond to those natively occurring in the ECM tissue, but perhaps of a different species (e.g. human proteins applied to collagenous ECMs from other animals, such as pigs). The non-native bioactive components may also be drug substances. Illustrative drug substances that may be incorporated into and/or onto the ECM materials include, for example, antibiotics or thrombus-promoting substances such as blood clotting factors, e.g., thrombin, fibrinogen, and the like. These substances may be applied to the ECM material as a premanufactured step, immediately prior to the procedure (e.g., by soaking the material in a solution containing a suitable antibiotic such as cefazolin), or during or after delivery of the material in the patient.

Submucosa or other ECM tissue used in the invention is preferably highly purified, for example, as described in U.S. Pat. No. 6,206,931, which is incorporated by reference herein in its entirety. Thus, preferred ECM material will exhibit an endotoxin level of less than about 12 endotoxin units (EU) per gram, more preferably less than about 5 EU per gram, and most preferably less than about 1 EU per gram. As additional preferences, the submucosa or other ECM material may have a bioburden of less than about 1 colony forming units (CFU) per gram, more preferably less than about 0.5 CFU per gram. Fungus levels are desirably similarly low, for example less than about 1 CFU per gram, more preferably less than about 0.5 CFU per gram. Nucleic acid levels are preferably less than about 5 $\mu$g/mg, more preferably less than about 2 $\mu$g/mg, and virus levels are preferably less than about 50 plaque forming units (PFU) per gram, more preferably less than about 5 PFU per gram. These and additional properties of submucosa or other ECM tissue taught in U.S. Pat. No. 6,206,931 may be characteristic of the submucosa tissue used in the present invention.

Preferred type of submucosa is derived from the intestines, more preferably the small intestine, of a warm blooded vertebrate; i.e., small intestine submucosa (SIS). SIS is commercially available from Cook Biotech, West Lafayette, Ind.

Preferred intestine submucosal tissue typically includes the tunica submucosa delaminated from both the tunica muscularis and at least the luminal portions of the tunica mucosa. In one example the submucosal tissue includes the tunica submucosa and basilar portions of the tunica mucosa including the lamina muscularis mucosa and the stratum compactum. The preparation of intestinal submucosa was described in U.S. Pat. No. 4,902,508, and the preparation of tela submucosa was described in U.S. Pat. No. 6,206,931, both of which are incorporated herein by reference. The preparation of submucosa was also described in U.S. Pat. No. 5,733,337 and in 17 Nature Biotechnology 1083 (November 1999); and WIPO Pub. WO 98/22158, which is the published application of PCT/US97/14855. Also, a method for obtaining a highly pure, delaminated submucosa collagen matrix in a substantially sterile state was previously described in U.S. Pub. No. 2004 0180042 A1, disclosure of which is incorporated by reference.

The ECM material may be processed to provide preferred shape or form of the ECM material. For example, the ECM material may take many shapes and forms, such as string or fiber-like, filament, thread, coiled; helical; spring-like; randomized; branched; sheet-like; tubular; spherical; fragmented; powdered; ground; sheared; fluidized; sponge-like; foam-like; and solid material shape.

While naturally derived biomaterials, particularly bioremodelable materials like SIS described above, are generally preferred, synthetic materials, including those into which growth factors are added to make them bioremodelable, are also within the scope of this invention.

In certain embodiments, an embolic protection device or other suitable device may also be used to filter and remove the cellular debris dislodged during the process of injuring the tissue.

In one embodiment, implantable medical devices in combination with various drugs, agents and/or compounds which further promote wound healing and endothelialization, and thereby reduce the risk of endoleaks or other similar phenomena, of the medical device may also be used for implantation following agitation and injury to the native tissue. Drug-coated implantable medical devices are known in the art.

EXAMPLES

Background

Biofixation feasibility study was performed to determine whether using SIS-enhanced Dacron graft could promote cell infiltration where the graft contacts natural vessel wall, so that a biological sealing and fixation can be achieved.

4 phases of animal studies were performed using a one-month porcine model and graft segments (8-10 mm OD×14-15 mm length) with the following configurations:
1. Plain Dacron as a Control;
2. Transversely arranged Nitinol stitching on Dacron;
3. Abluminal SIS sheet covering the Dacron fabric with Nitinol looped stitches;
4. Abluminal SIS gel covering the Dacron fabric with Nitinol looped stitches;
5. Transversely arranged silk stitching on Dacron;
6. Abluminal SIS sheet covering the Dacron fabric with silk stitches;
7. Transversely arranged SIS hand stitch on Dacron; and
8. Abluminal SIS sheet covering the Dacron fabric with Nitinol stitches and barbs.

Method:

To determine how SIS promotes tissue ingrowth in endovascular graft, a porcine model was employed and a pull test was performed. For each junior pig, two graft samples were implanted in its left and right iliac arteries using a standard protocol. During the implantation the arteries were slightly overextended in order to implant the grafts. The animals were sacrificed one month after implantation.

Pull Test:

A bench top pull test was designed and performed for each phase of animal study. Specifically, the pull test was performed by pulling the stent longitudinally out of the explants. One end of the artery was attached to the fixture of the testing machine, and suture threads were attached to the stent itself so that the pull force is simply the attachment force between stent and native artery.

As illustrated in Tables 1-6 below, all the pull tests indicated that SIS sheet with nitinol stitched Dacron produced the highest pull-out force, which is approximately 90% higher than Dacron control.

TABLE 1

| Specimen # | Description of Specimen | Pull Force (N) | Comments |
|---|---|---|---|
| 1 | Dacron + SIS sheet + niti stitch | 15.28 | Pulls OK |
| 2 | Dacron + SIS gel + niti stitch | 18.28 | Vessel necks, no pullout |
| 3 | Dacron Control | 9.15 | Pulls OK |
| 4 | Dacron + SIS sheet + niti stitch | 15.28 | Pulls OK |
| 5 | Dacron + SIS sheet + niti stitch | 13.96 | Pulls OK |
| 6 | Dacron + SIS gel + niti stitch | 8.14 | Pulls OK |
| 7 | Dacron + SIS gel + niti stitch | 13.28 | Pulls OK |
| 8 | Dacron Control | 8.96 | pull out OK |
| 9 | Hand sewing SIS fiber | 10.34 | pull out OK |
| 10 | Hand sewing SIS fiber | 15.35 | pull out OK |
| 11 | Dacron + SIS sheet + niti stitch | 16.1 | pull out OK |
| 12 | Dacron + SIS sheet + niti stitch | 17.6 | pull out OK |
| 13 | Dacron Control | 6.72 | pull out OK |
| 14 | Silk stitch + Dacron | 10.4 | pull out OK |
| 15 | Nitinol stitch + Dacron | 11.43 | pull out OK |
| 16 | Silk stitch + Dacron | 12.97 | pull out OK |
| 17 | Silk stitch + SIS sheet + Dacron | 12.41 | pull out OK |

TABLE 1-continued

| Specimen # | Description of Specimen | Pull Force (N) | Comments |
|---|---|---|---|
| 18 | Nitinol stitch + Dacron | 11.79 | pull out OK |
| 19 | Silk stitch + SIS sheet + Dacron | 11.44 | pull out OK |

TABLE 2

Statistical Analysis

| Article Description | Averaged Peak Force (N) | Percentage Increase (%) |
|---|---|---|
| Dacron Control (3) | 8.28 (from 6.7 to 9.1) | 0 |
| SIS sheet + niti stitch (5) | 15.64 (from 14.0 to 17.6) | 89.01329037 |
| SIS gel + niti stitch (3) | 13.23 | 59.88723319 |
| Hand sewing SIS fiber (2) | 12.85 | 55.19532823 |
| Silk stitch (2) | 11.69 | 41.18002416 |
| Silk stitch + SIS sheet (2) | 11.93 | 44.07974225 |
| Niti stitch (2) | 11.61 | 40.27386226 |

Dacron Control Vs. SIS Sheet/Niti Stitched Dacron

Phase 1 Pull Test:

TABLE 1

| Specimen # | Description of Specimen | Pull Force (N) | Comments |
|---|---|---|---|
| 1 | SIS Sheet, Right iliac | 15.28 | Pulls OK |
| 3 | Control, Right iliac | 9.15 | Pulls OK |
| 4 | SIS sheet, Left iliac | 15.28 | Pulls OK |

Phase 2 Pull Test:

TABLE 2

| Specimen # | Description of Specimen | Pull Force (N) | Comments |
|---|---|---|---|
| 5 | SIS Sheet, Left iliac | 13.96 | Pulls OK |

Phase 3 Pull Test:

TABLE 3

| Specimen # | Article Description | Peak Pull Force (N) | Comment |
|---|---|---|---|
| 479R | Dacron Control | 8.96 | pull out OK |
| 480L | Dacron + SIS sheet + niti stitch | 16.1 | pull out OK |
| 478R | Dacron + SIS sheet + niti stitch | 17.6 | pull out OK |
| 478L | Dacron Control | 6.72 | pull out OK |

Phase 4 Pull Test (Soaked in Formalin, Biased Data):

TABLE 4

| Specimen ID | Specimen Description | Maximum Load (N) |
|---|---|---|
| 1 | 279L | SIS niti barb | 25.98 |
| 2 | 279R | Control | 26.92 |
| 3 | 281L | Control | 18.72 |
| 4 | 281R | SIS niti barb | 27.48 |
| 5 | 283L | SIS niti barb | 31.52 |
| 6 | 283R | SIS niti barb | 40.30 |

Histology Analysis:

Histology analysis was performed using the samples from each phase.

Histology report indicated that the internal elastic lamina (IEL) was intact for phase 1 and 2, but severely damaged for phase 3 possibly due to oversizing of the implants.

Figure 7:
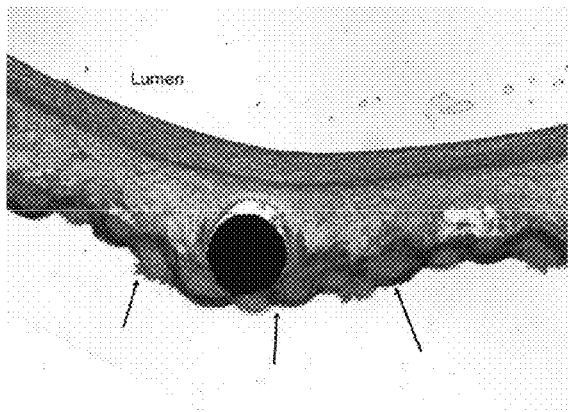
FIG. 7A-B is a picture of a histology slide of Dacron control grafts.
Figure 7:
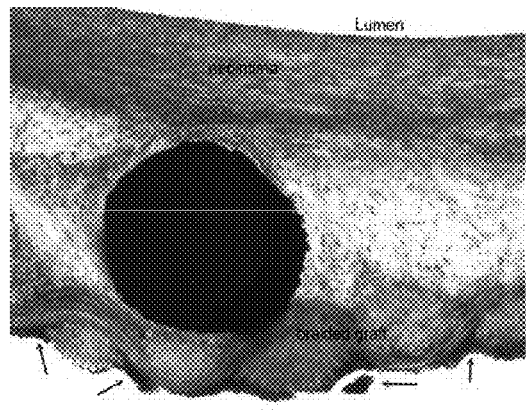

Histology analysis was also performed for the pulled out samples of phase 3, including Dacron controls, nitinol stitched SIS sheet sample, and hand stitched SIS fiber. Both Dacron controls showed no cells peripheral to the graft, as shown in FIG. 7. Specifically, FIG. 7 illustrates 478 L and 479R graft pulled from artery at 40×(A) and 100×(B). Arrows point to minimal tissue adhered to the peripheral surface of the braided graft.

Figure 8:
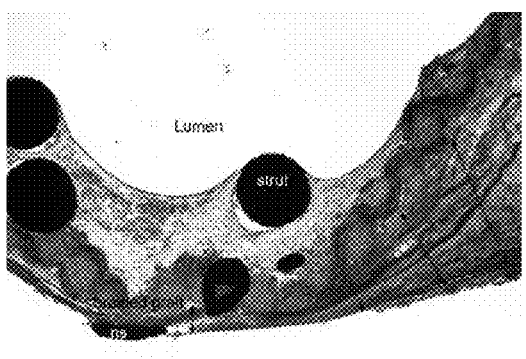
FIG. 8A-B is a picture of a histology slide of nitinol stitched SIS grafts.
Figure 8:
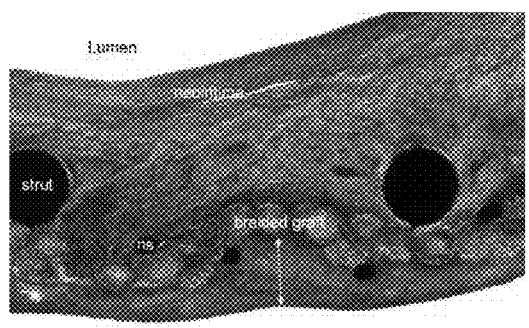

Both nitinol stitched SIS specimens were infiltrated by a thick layer of tissue on the peripheral circumference of the graft, as shown in FIG. 8. Specifically, FIG. 8 illustrates 480L and 478 R graft pulled from artery at 40×. Layer of intima peripheral to the braided graft (dotted arrow) is mostly granulation tissue heavily infiltrated with lymphocytes and macrophages. Nitinol stitch (ns).

It is believed that this thick layer of tissue leads to the consistent high forces during those pull tests.

CONCLUSIONS

Based on this feasibility animal study, it can be seen that SIS enhanced Dacron graft (specifically SIS sheet and nitinol stitch) leads to a thick layer of tissue peripheral to the graft, which may be the reason for its much higher pull out force (an indication of biological fixation). This thick layer of tissue can also lead to an effective biological sealing. More importantly, due to its thrombogenicity, the added SIS layer may provide an immediate sealing to mitigate acute type I endoleak.

Also, oversizing or overextension of the vessel (i.e., injury) which occurred during phase 3 of the animal studies during implantation of the grafts lead to enhanced proliferation and cell ingrowth observed with the implanted grafts.

It is therefore intended that the foregoing detailed description be regarded as illustrative rather than limiting, and that it be understood that it is the following claims, including all equivalents, that are intended to define the spirit and scope of this invention.

The invention claimed is:

1. A method of promoting cell proliferation and ingrowth around an implantable medical device, comprising:
   a) inserting an apparatus, the apparatus comprising asperities adapted to injure native tissue at a desired anchoring location;
   b) inserting the apparatus to dislodge cellular debris at the desired anchoring location prior to injuring the native tissue;
   c) injuring the native tissue with the apparatus at the desired anchoring location to thereby initiate an injury response in the native tissue to promote cell proliferation and ingrowth; and
   d) implanting the device at the treatment location.

2. The method of claim 1, wherein the apparatus is integrated with a delivery system.

3. The method of claim 1, wherein the apparatus is selected from the group consisting of an inflatable device, a self-expandable device, and a laser.

4. The method of claim 3, wherein the inflatable device is a balloon.

5. The method of claim 3, wherein the self-expandable device is a stent or a filter.

6. The method of claim 1, wherein the asperities comprise sharp tips.

7. The method of claim 1, wherein the step of injuring comprises moving the apparatus proximally and distally at the anchoring location or rotating the apparatus at the anchoring location.

8. The method of claim 1, wherein the apparatus comprises radiopaque material.

9. The method of claim 1, wherein the device is a graft or a stent graft.

10. The method of claim 1, wherein the device comprises a naturally derived collagenous material.

11. The method of claim 1, wherein the native tissue is an aortic tissue.

12. A method of promoting cell proliferation and ingrowth around an implantable medical device to treat an aneurysm, comprising:
   a) inserting an apparatus, the apparatus comprising asperities adapted to injure native tissue at a desired anchoring location near the aneurysm;
   b) inserting the apparatus to dislodge cellular debris at the desired anchoring location prior to injuring the native tissue;
   c) injuring the native tissue with the apparatus at the desired anchoring location to thereby initiate an injury response in the native tissue to thereby promote cell proliferation and ingrowth; and
   d) implanting the device at an aneurysm location.

13. The method of claim 12, wherein the step of injuring comprises moving the apparatus proximally and distally at the aneurysm location or rotating the apparatus at the aneurysm location.

14. The method of claim 12, wherein the aneurysm is an abdominal aortic aneurysm.

15. The method of claim 12, wherein the apparatus is integrated with a delivery system.

16. The method of claim 12, wherein the apparatus is selected from the group consisting of an inflatable device, a self-expandable device, and a laser.

17. The method of claim 16, wherein the inflatable device is a balloon.

18. The method of claim 16, wherein the self-expandable device is a stent or a filter.

* * * * *